United States Patent [19]
Dormia

[11] Patent Number: 5,380,335
[45] Date of Patent: Jan. 10, 1995

[54] APPARATUS FOR EXPELLING FOREIGN BODIES IN AN ELONGATED ORGAN OF A LIVING ORGANISM

[75] Inventor: Guido Dormia, Lecco, Italy

[73] Assignee: Angiomed AG, Karlsruhe, Germany

[21] Appl. No.: 960,687

[22] Filed: Oct. 14, 1992

[30] Foreign Application Priority Data

Feb. 28, 1992 [IT] Italy .................. MI92A-000449

[51] Int. Cl.6 .................................. A61B 17/22
[52] U.S. Cl. .................. 606/127; 604/264; 623/11
[58] Field of Search ............ 606/127, 128; 604/264, 604/266, 281; 128/24 EL; 623/11, 66

[56] References Cited

U.S. PATENT DOCUMENTS

| 4,776,844 | 10/1988 | Ueda | 604/281 |
| 4,813,925 | 3/1989 | Anderson, Jr. et al. | 604/281 |
| 5,055,101 | 10/1991 | McCoy | 604/95 |
| 5,129,910 | 7/1992 | Phan et al. | 606/127 |

FOREIGN PATENT DOCUMENTS

| 391384 | 10/1990 | European Pat. Off. | 606/127 |
| 3312672 | 10/1984 | Germany | 604/264 |

*Primary Examiner*—Tamara L. Graysasy
*Attorney, Agent, or Firm*—Antonelli, Terry, Stout & Kraus

[57] ABSTRACT

An apparatus for separating foreign bodies in an elongated organ of a living organism such as a ureter. A collection of stone fragments, such as, for example, kidney stones are crushed by lithotrite and, to prevent accumulation of the fragments an elongated element is provided with the elongated element baffles.

9 Claims, 6 Drawing Sheets

APPARATUS FOR EXPELLING FOREIGN BODIES IN AN ELONGATED ORGAN OF A LIVING ORGANISM

FIELD OF THE INVENTION

The invention relates to an apparatus for expelling foreign bodies, such as stone fragments, through an elongated organ of a living organism, such as in the ureter.

BACKGROUND OF THE INVENTION

For the destruction of stones or calculi in the organs of a living organism, such as in particular the kidneys of a human body, use is made of suitable apparatuses for emitting pressure waves, namely lithotrites. The pressure waves ensure that the stones are broken up into fragments. The stones are then expelled through the ureter, the bladder and finally the urethra from the body.

The fragments tend to move virtually simultaneously through the ureter and to form a closure or obstruction therein. It has been found that the obstruction frequently forms at the end of the ureter, where the latter projects into the bladder, because in this terminal portion the ureter passage is narrowed. In such cases it is difficult and painful to remove the stones and an operation is unavoidable.

Due to the obstruction, the urine which has formed within the kidney cannot be expelled from the ureter, because the obstruction acts like a "plug" and consequently the liquid collects in the ureter, swells the walls of the latter and causes severe pain to the patient. There is also a damming back, which can dammage the kidney.

This makes an operation necessary to remove such obstructions from the patient. Such an operation can be performed endoscopically. For this purpose initially an endoscope with an optical fibre is introduced in order to locate the obstruction, which is then removed through another tube or catheter. It can occur that such an obstruction is very compact, so that the tissue of the ureter must be cut, in order to widen the passage and remove the fragments.

It has been observed that particularly stone fragments having the size of dust tend to produce an obstruction within the ureter. Such small fragments collect more easily and are more easily bound together than the larger, coarser fragments.

Therefore the removal of kidney stones can take a long time and be based on considerable effort, which can be painful and unpleasant for the patient.

SUMMARY OF THE INVENTION

The aim underlying the invention resides in providing an apparatus, which avoids the formation of such obstructions in the ureter and by which, if necessary, should an obstruction still form in a particular case, it can be easily and painlessly removed.

The invention includes an elongated element, which is provided with baffles in order to individualize or separate the foreign bodies such as, for example, stones.

In addition to the individualization or separation of stones, the apparatus according to the invention has the advantage that it simultaneously forms a ureter stent preventing a urine backflow, so that reinfection is prevented. The length of the inventive apparatus can be appropriately adapted to different ureter lengths. Both the elongated element and the baffles can have different diameters. Preferably the apparatus can also be constructed as an endoprosthesis with an end projecting out of the bladder.

The baffles can be in the form of spaced thickened portions provided on the elongated, wire-like element. The thickened portions can be spherical or hemispherical. They can be in the form of two cones joined at their base. They can also be disk- or drop-shaped.

Through the construction of the apparatus according to the invention between two baffles or thickened portions a free space is left for the temporary reception of stone fragments. This ensures a reliable separation of the stone fragments over the length of the inventive apparatus and therefore the length of the elongated organ, such as in particular the ureter. The formation of obstructions is made virtually impossible as a result of this separation.

In a preferred embodiment the elongated element is formed from metal wire and according to an advantageous, patient-protecting embodiment the elongated element is made from memory metal.

According to a-further embodiment the front sides of the elongated element are provided with thickened portions, particularly if the front, distal end and/or the rear, proximal end of the elongated element is bent in an at least semiarcuate manner or the front and/or rear end of the elongated element is bent in spiral manner. This reliably prevents injury to the kidney system or to the bladder wall.

According to a further embodiment the baffles and/or thickened portions contain roentgen-opaque material, the latter being, for example, bismuth carbonate.

BRIEF DESCRIPTION OF THE DRAWINGS

Further advantages and features of the invention can be gathered from the claims and following specific description of an embodiment of the invention relative to the drawings, wherein:

DETAILED DESCRIPTION

Figure 1:
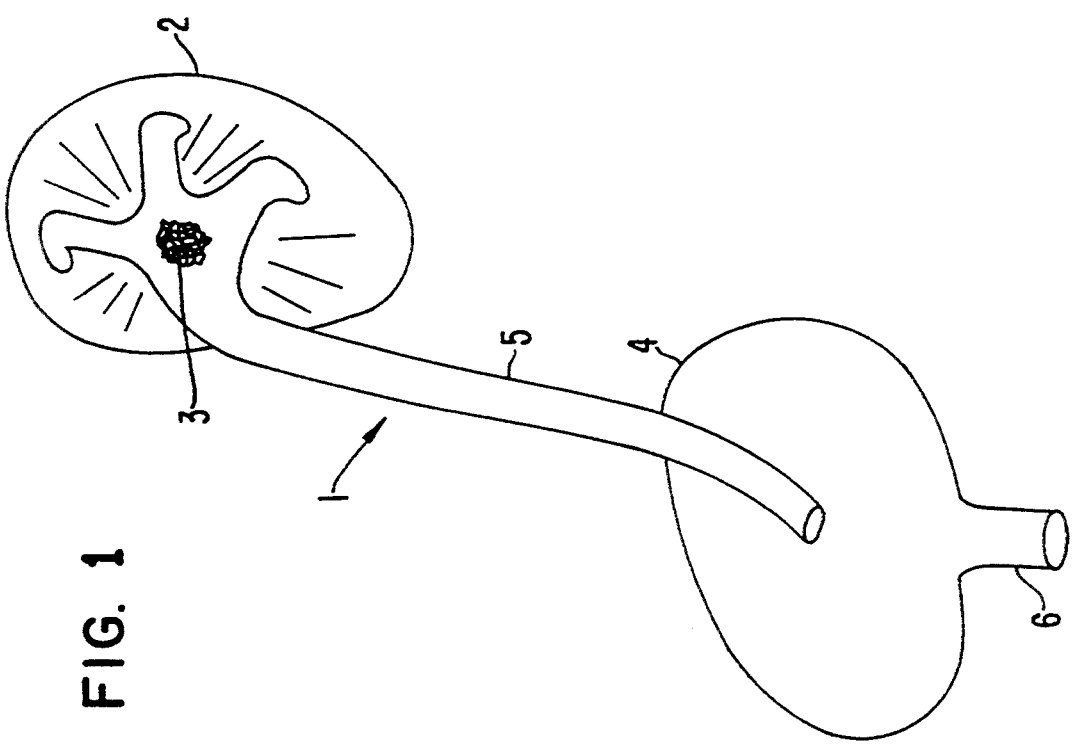
FIG. 1 is schematic view of urinary organs of a human body with a stone or calculus shown in the kidney.
Figure 4:
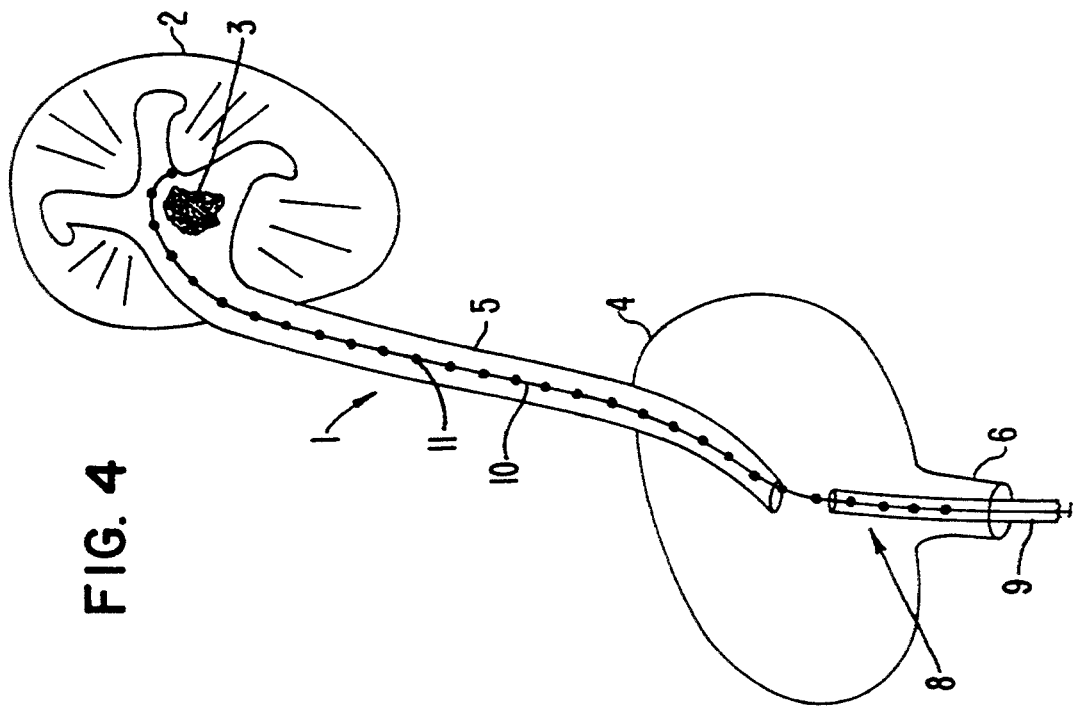
FIG. 4 is a schematic view of the inventive apparatus in the working position prior to a destruction of the stone.

FIG. 1 schematically depicts urinary organs 1 of a human body, with a first organ being a kidney 2 having a kidney stone 3. The kidney 2 is connected to the bladder (vesica urinalis) 4 by the ureter 6, which projects somewhat into the bladder 4, which leads to the urethra 6.

Figure 2:
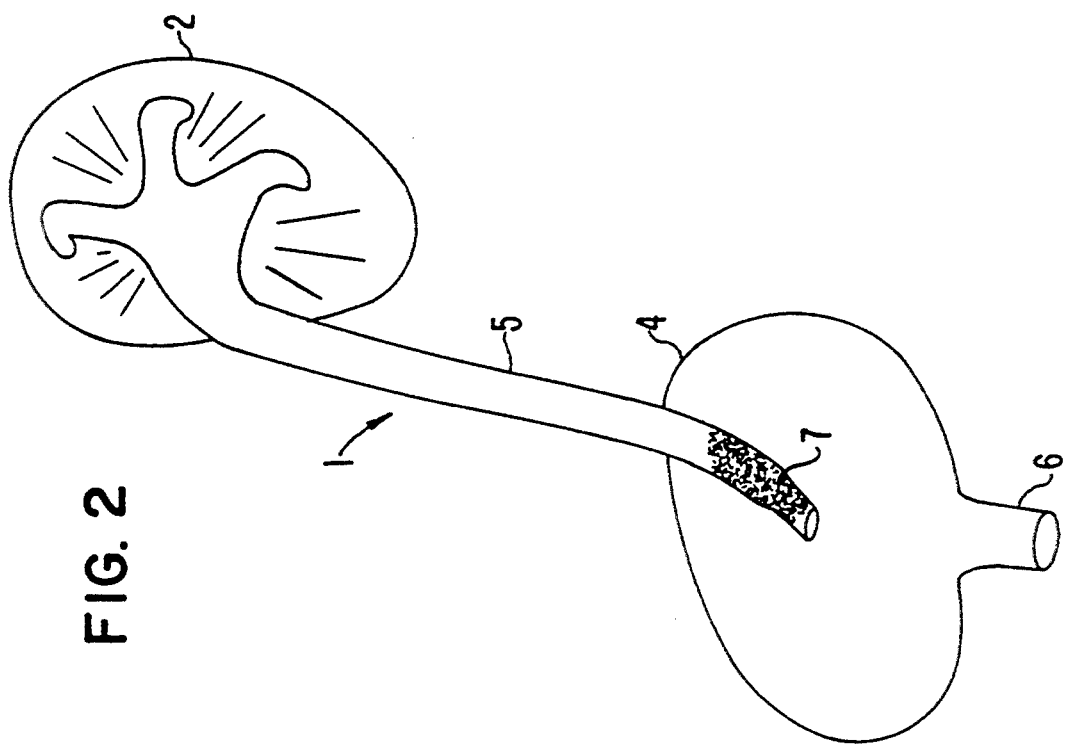
FIG. 2 is a schematic view of an obstruction at a lower end of the ureter formed by fragments of the stone shown in FIG. 1.

Following the destruction of a stone, for example, a kidney stone, in a human body, it may occur that the stone fragments 7 (FIG. 2) passing out of the organ through a corresponding duct, such as the ureter 5, collect in the duct and can obstruct the latter, i.e. form an obstruction or closure. In particular, fine dust-size particles can bond together again to form large stone fragments. It is difficult to remove such an obstruction and an operation may be required. This is the starting point of the invention.

In the illustrated embodiment, the apparatus according to the invention a wire 10 includes, for example, spaced baffles located thereon in the form of spherical thickened portions 11. The wire 10 is preferably made from stainless steel, which has an appropriate rigidity and flexibility. Instead of being formed by the metal wire 10, the elongated element could also be a wire made from plastic, glass, carbon or aramide fibres. The elongated element may also be a solid part or may be helically formed from a fiber, with the engaging turns having a limited pitch. Instead of this, the elongated element may be formed by helically connected individual fibers or strands. The thus formed elongated element may, as a result of its inherent rigidity, instead of having the shape shown in FIG. 3, pass over part of its length, namely, in the ureter 5, in the form of helical turns, which have a finite spacing, so as to bring about a wider opening of the ureter 5 which forms a muscular-membranous tube and to ensure a free passage within the turns. The elongated 10 extends from the kidney 2 to outside the human body. As shown in the drawing, the baffles 11 can be spherical thickened portions on the extended connecting part. However, they can also be hemispherical, disk-shaped or drop-shaped thickened portions. The thickened portions can also be in the form of a double cone, i.e. two cones joined by their base. The thickened portions can also be made from the most varied materials, such as metal, particularly stainless steel, particularly if the elongated element is also made from stainless steel, plastic or the like.

According to a preferred embodiment the baffles 11 comprise small acrylate or dimethyl acrylate balls fixed in a spaced manner to the elongated element and with which is, in each case, admixed bismuth carbonate in order to bring about the desired roentgen-opaqueness.

Particularly if the elongated element is guided helically with spaced individual turns, it is preferable to use a memory metal, which is so prestressed that the elongated element is elongated at low introduction temperature and only assumes the helical shape in its prestressed high temperature position.

Figure 3:
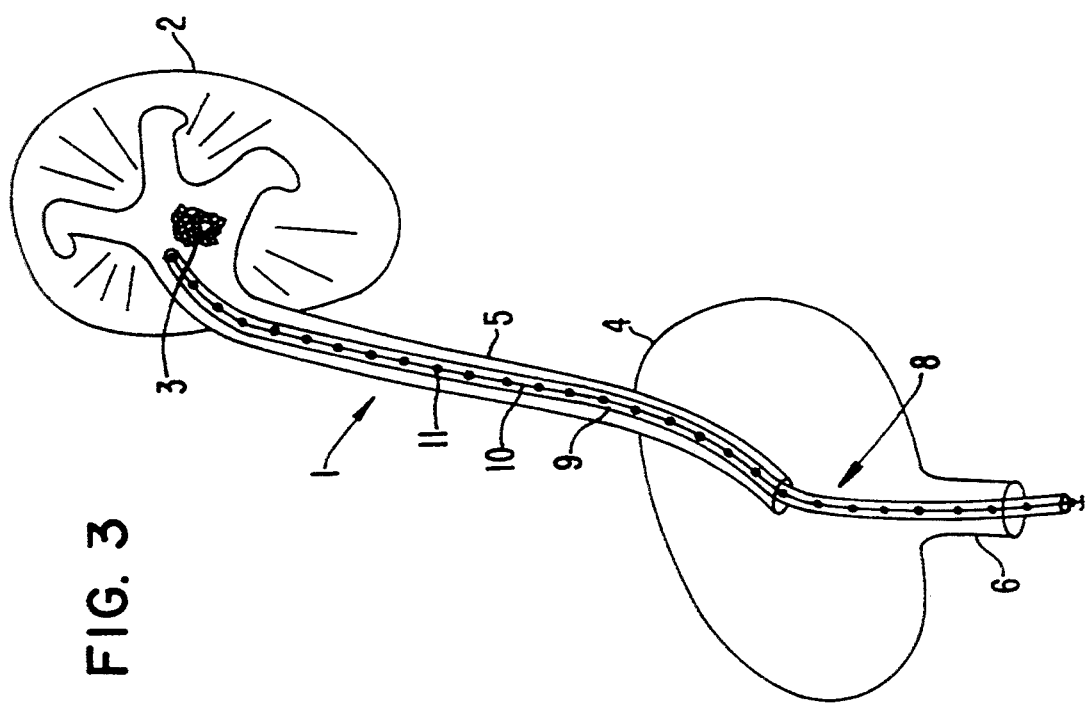
FIG. 3 is a schematic view of the inventive apparatus in the urinary organs of the human body with an insertion catheter.
Figure 7:
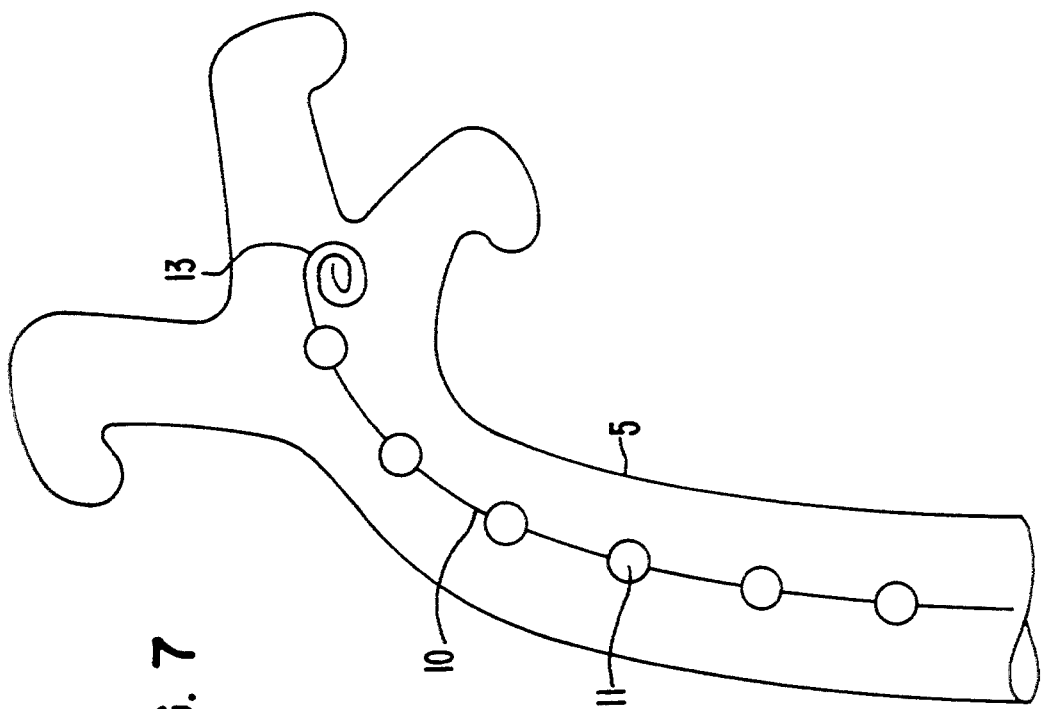
FIG. 7 is a representation of the upper region of FIG. 4, on an enlarged scale.
Figure 9:
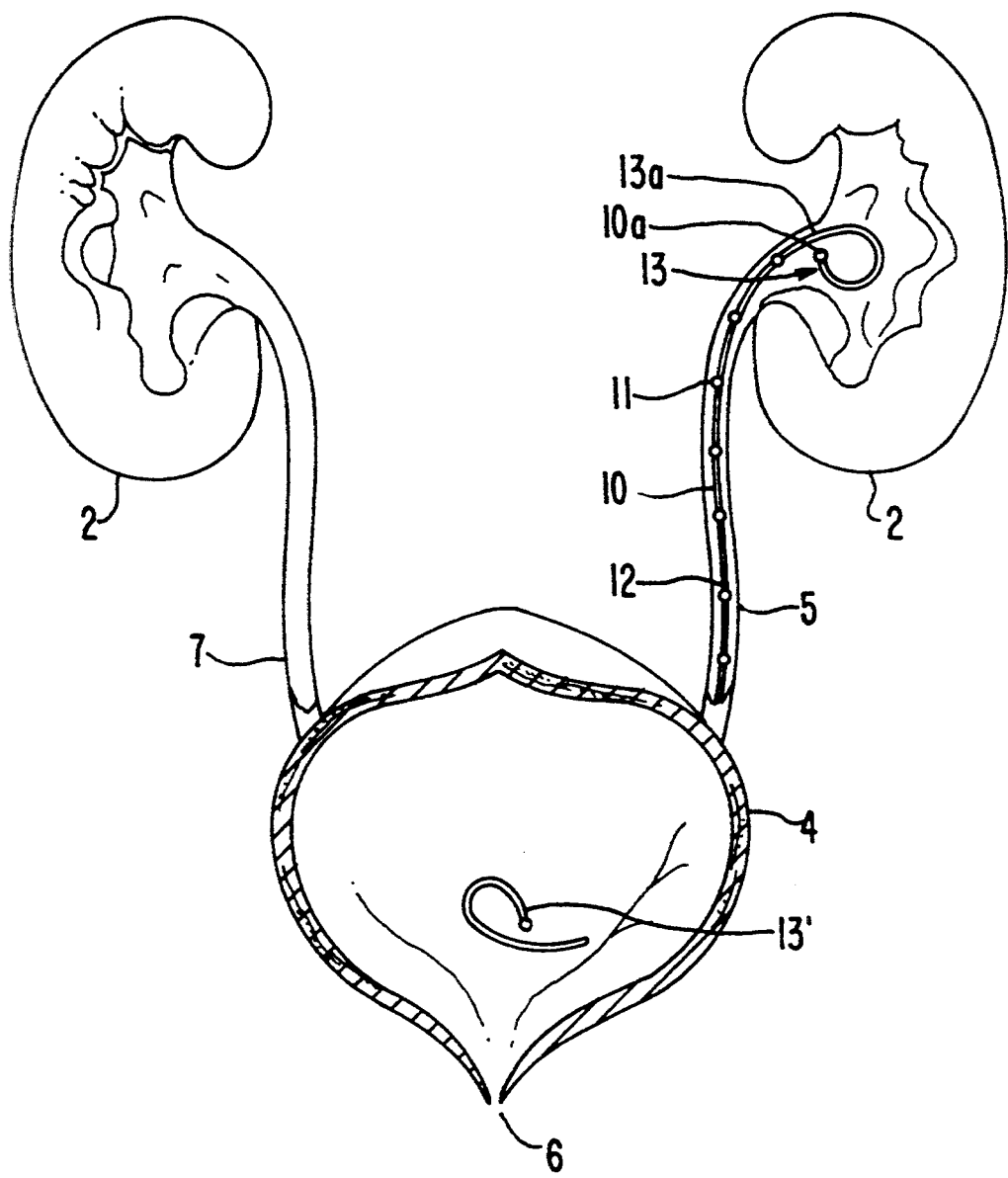
FIG. 9 is a schematic representation of the urinary organs with an obstruction in the left ureter, as prevented by the apparatus for separating stone fragments according to the present invention located in the right ureter.

The inventive apparatus 8 formed from an elongated element 10 with thickened portions 11 arranged in spaced manner thereon is preferably introduced by a very elastic plastic catheter 9 into the ureter 5, as shown in FIG. 3. As the front of the catheter 9 must be open, because it must subsequently be drawn over the apparatus 8 according to the invention, the catheter 9 itself is introduced by the Seldinger guide-wire technique. After installing the catheter 9 it permits the introduction of the apparatus 8 with the elongated connecting part 10 and the thickened portions 11 until the front end 13 reaches the kidney 2. When the front end 13 (FIG. 7) is passed out of the catheter 9 there, then it assumes an at least arcuate or spiral configuration, so as to form a securing means in the kidney 2, particularly on drawing out the catheter 9. The ends 13,13' of the elongated element 10, if the latter is made from wire, can be provided with a plastic envelope 10a. Thickened portions 13a can also be provided at the end faces (FIG. 9). The catheter 9 is subsequently removed from the ureter 5.

It is then possible to crush the stones by pressure waves produced by a lithotrite. Then, in the manner shown in FIG. 5, the individual stone fragments 7 are moved by the urine formed in the kidney 2 out of the latter through the ureter 5, past the wire 10 and thickened portions 11 and initially into the bladder 4. The individual stone fragments 7 do not slide in agglomerated form through the ureter 5 and instead, during their movement through the latter, the fragments 7 are separated and are partly held back for a varying period of time over the entire length of the apparatus in the gaps between the individual thickened portions 11, which bring about changes to the free ureter cross-section, so that they are initially distributed over the entire length of the inventive apparatus.

Figure 8:
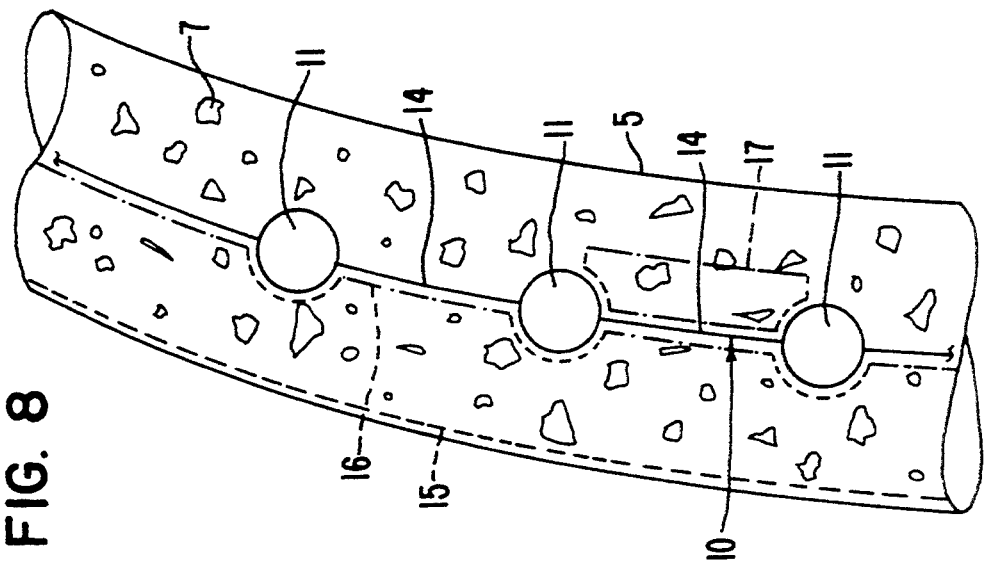
FIG. 8 is a representation of a central region of FIG. 5, on an enlarged scale.

FIG. 8 shows that each pair of successive thickened portions 11 and the portions 14 of the wire 10 located between the successive thickened portions 11 form areas which separate the fragments 7, in that the fragments 7 are temporarily collected in these areas and, consequently, undergo different delays in their movements. One of these areas is symbolized by the closed dot-dash line and is designated by the reference numeral 17 in FIG. 8.

In the case of the embodiment of the wire 10, fragments 7 moving close to the line 15 along the wall of the ureter 5 can slide downwardly in a substantially unhindered manner, but do not move linearly, but instead partly migrate towards the inside of the ureter 5. In the latter the stone fragments 7 moving close to the wire 10 and thickened portions 11 and roughly follow the line 16, with the stone fragments 7 being delayed in their movement as compared with the previously described stone fragments by the baffles or thickened portions 11 and must also pass round the baffles or thickened portions 11, so that the fragments 7 also have a long travel path. In this way, as a function of the particular wire shape, part of the fragments 7 will move faster and follow a shorter route along the ureter 5 in order to reach the bladder 4 first. On the other side, part of the fragments 7 will move more slowly and take a longer route and therefore will subsequently reach the interior of the bladder 4.

Figure 5:
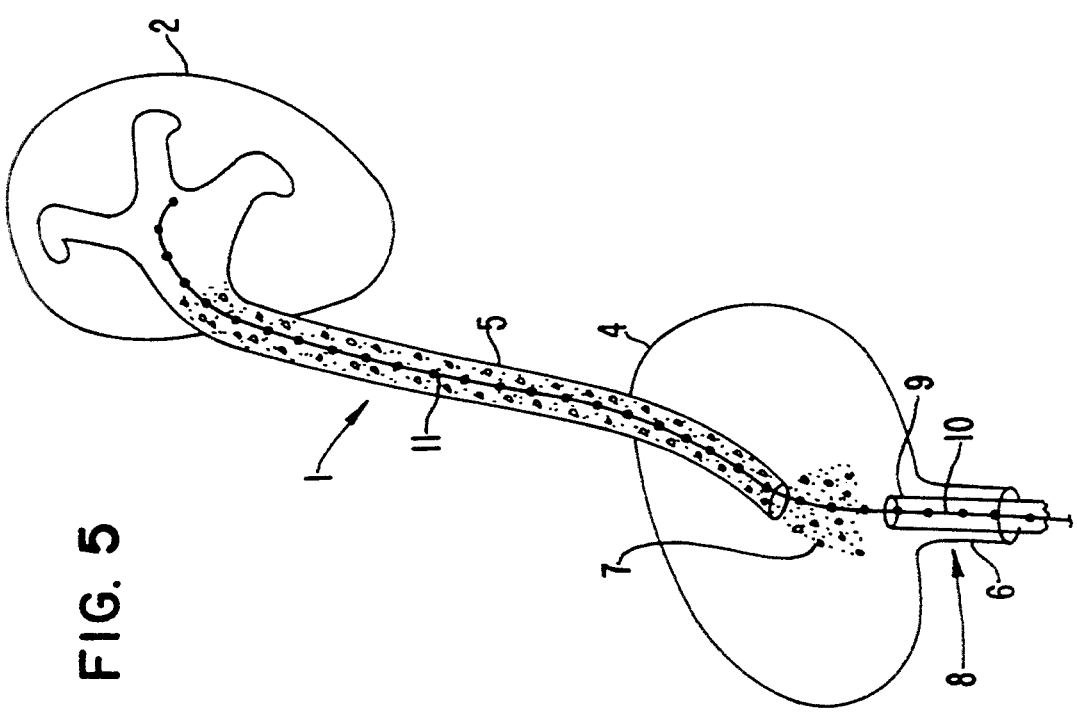
FIG. 5 is a schematic view of the inventive apparatus following a breaking open of the stone.

Thus, as has been surprisingly found, there is a very good separation or individualization of the stone fragments 7 over the entire length of the ureter 5 and the inventive apparatus 8, as is in particular shown in FIG. 5. The formation of obstructions is prevented, because the fragments 7 move differently and not simultaneously through the ureter 5, as shown most clearly in FIG. 9.

Figure 6:
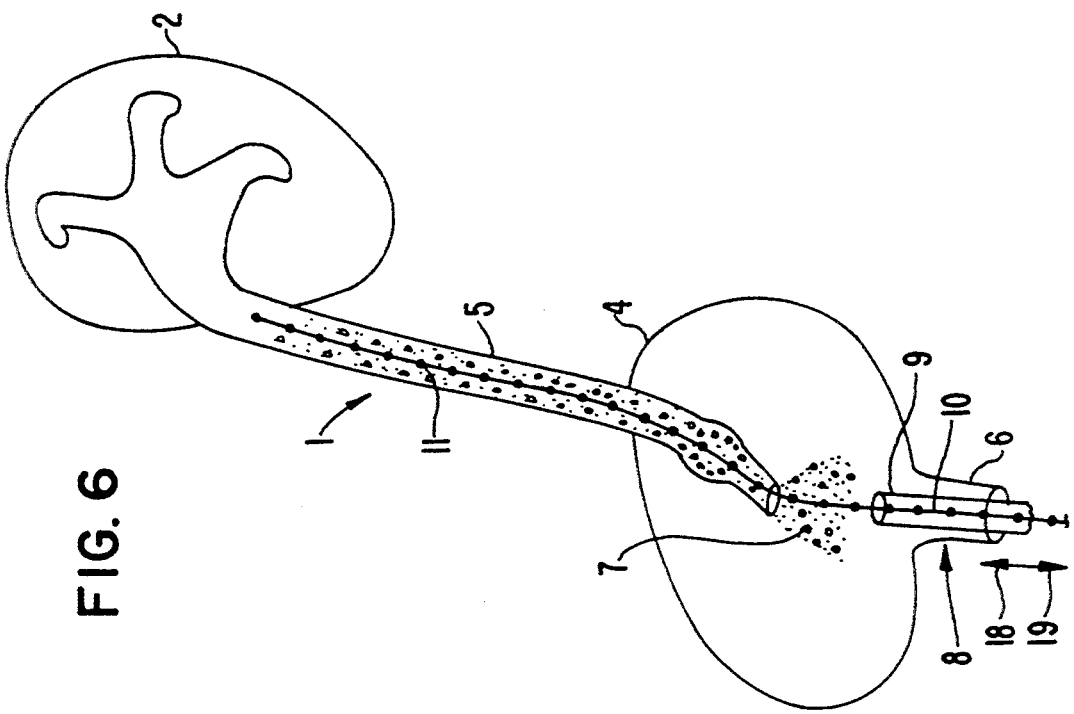
FIG. 6 is a schematic representation of the manner by which an accumulation of stone fragments formed in the ureter can be removed.

However, if an accumulation of stone fragments 7 at the lower end of the ureter 5 in the manner shown in FIG. 6 incurs, the accumulated fragments 7 can easily be removed in that the wire 10 and the thickened portions 11 are axially moved rearwardly and forwardly from the outside, as shown by the arrows 18 and 19 respectively, so that the collected stone fragments 7 are moved out of the lower ureter 5 opening into the bladder 4. These forward and rearward movements of the wire 10 leads to a loosening of the fragments 7 forming the obstruction and, consequently, free the passage through the ureter 5. This is possible because, as has been already established, the wire 10 is made from a material having a certain flexibility, which permits an easy insertion, together with the catheter 9, into the human body, but at the same time there is a certain rigidity, which makes it possible to move the wire 10 within the ureter 5, without the wire 10 being compressed in an undulatory or corrugated manner.

It has been found that the apparatus according to the invention greatly reduces the risk of cluster formations within the ureter 5, particularly in the lower region of the ureter 5 and stone fragments 7 only rarely accumulate. It has also been found that these collections of fragments 7 can be removed in the manner described above, which avoids the need for operations, such as have frequently been necessary with cluster formations up to now.

The use of the apparatus according to the invention is not restricted to stones formed within the kidney 2, but is also applicable to stones formed within the bladder 4. Instead of introducing the apparatus into the ureter 5, in this case the apparatus is adequate to introduce it into the urethra 6, before crushing the stones by the application of pressure waves. Then, as described hereinbefore, the apparatus is used for removing the stone fragments 7 from the kidney 2 and the bladder 4 respectively.

Figure 10:
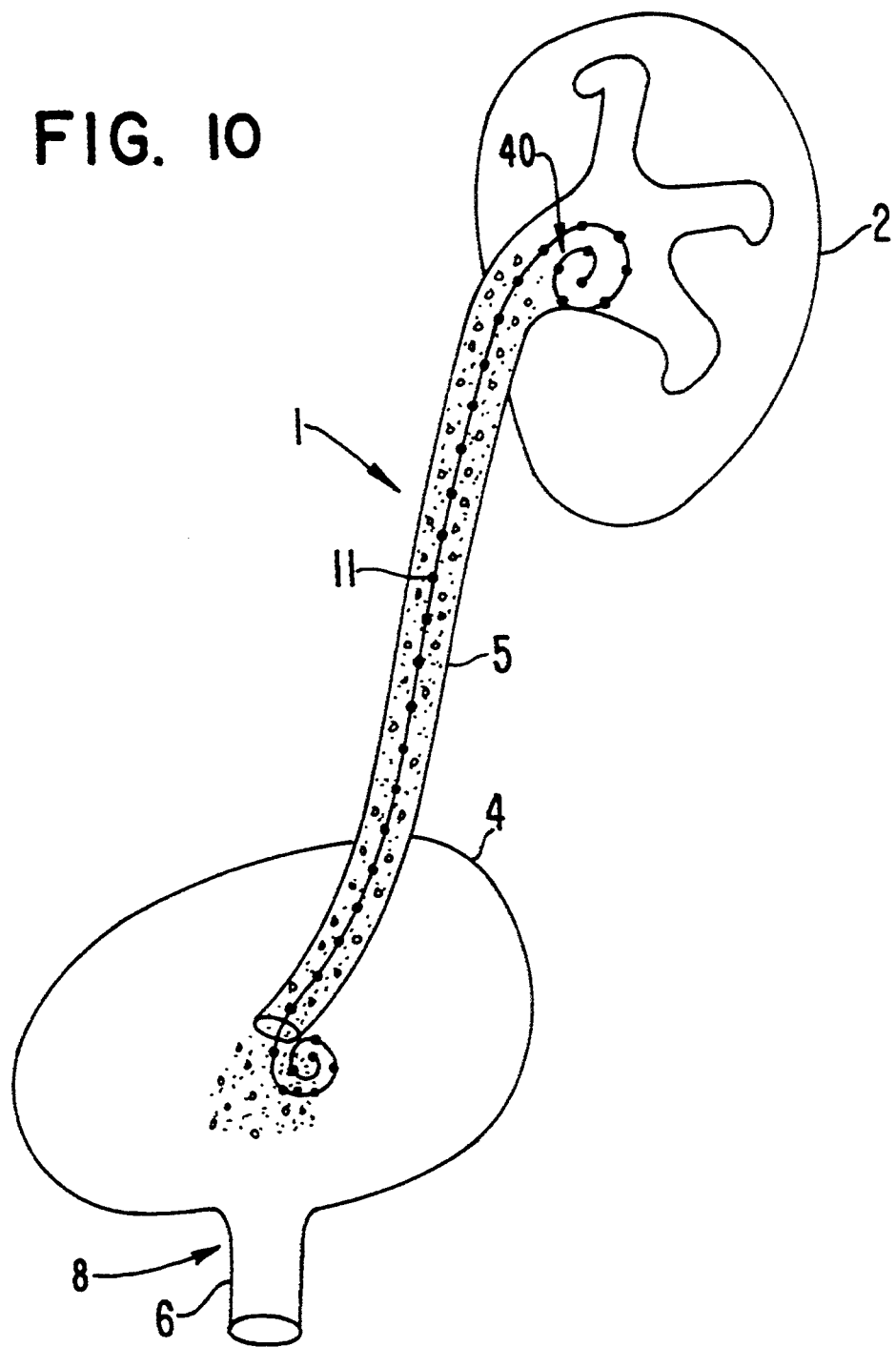
FIG. 10 is a schematic view of urinary organs of a human body depicting the manner by which an accumulation of stones formed in the ureter can be removed in accordance with another embodiment of the present invention.

As shown in FIG. 10, at least one of a distal end 40 and a proximal end 41 may be bent in a spiral manner. Moreover, in accordance with the present invention, the elongated element may be fashioned of fiber-reinforced material or, as noted above, fashioned of at least one of glass, armid or carbon fibers. Additionally, an internal diameter of the ureter 5 and a diameter of spherical members or thickened portions 11 may be in the range of 1:1 to 3:1.

I claim:

1. Apparatus for separating foreign bodies in an elongated organ of a living organism, the apparatus comprising an elongated element comprising a solid metal wire, and baffles provided on said solid metal wire and, said baffles comprising spherical members in order to enable a separation of the foreign bodies, and wherein respective ends of the elongated element include thickened portions.

2. Apparatus according to claim 1, wherein the elongated element provided with baffles is surrounded by a catheter.

3. Apparatus according to claim 2, wherein the solid metal wire is a memory metal.

4. Apparatus according to claim 1, wherein the solid metal wire is a memory metal.

5. Apparatus according to claim 1, wherein at least one of a distal and proximal end of the elongated element is at least bent in a semiarcuate manner.

6. Apparatus according to claim 1, wherein the elongated organ is a ureter, and wherein a ratio between an internal diameter of the ureter and a diameter of the spherical members is in a range of 1:1 to 3:1.

7. Apparatus according to claim 1, wherein at least one of the baffles and the thickened portions contain roentgen-opaque material.

8. A method for introducing a device for separating foreign bodies in an elongated organ of a life form, the method comprising the steps of:

providing a device having an elongated element comprising a solid metal wire, and baffles provided on said solid metal wire and comprising substantially spherical thickenings along the elongated element, a forward end of the metal wire includes a first thickened portion in the form of a partial arc, and a rear end of the metal wire includes a second thickened portion in the form of an arcuate portion, introducing a catheter into the elongated organ, inserting the forward end of the solid metal wire through the catheter into the elongated organ until the thickened portion at the forward end of the metal wire emerges from a forward end of the catheter and forms the partial arc, securing the partial arc in such a manner that the catheter can then be completely retracted, and retracting the catheter completely so that the thickened portion at the rear end of the metal wire emerges and forms the arcuate portion.

9. A method for separating accumulations of stone fragments in an elongated organ of a life form by a device for separating foreign bodies, the method comprising the steps of:

providing a device having an elongated element comprising a solid metal wire adapted to be moved in a forward and rearward direction and having disposed thereon a plurality of substantially spherical thickenings, said spherical thickenings also being provided at respective ends of the metal wire, inserting the device into the elongated organ, separating the accumulations of stone fragments by repeatedly moving the elongated element in the forward and rearward directions, and removing the stone fragments out of the elongated organ.

* * * * *